(12) United States Patent
Ouchi

(10) Patent No.: US 6,200,262 B1
(45) Date of Patent: Mar. 13, 2001

(54) FORCEPS STOPPER FOR ENDOSCOPE

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/268,333

(22) Filed: Mar. 16, 1999

(30) Foreign Application Priority Data

Mar. 17, 1998 (JP) .................................................. 10-066521

(51) Int. Cl.⁷ ...................................................... A61B 1/06
(52) U.S. Cl. .......................... 600/154; 600/159; 604/167
(58) Field of Search ................... 600/154, 159; 604/167

(56) References Cited

U.S. PATENT DOCUMENTS

| | | |
|---|---|---|
| 4,653,477 | 3/1987 | Akui et al. . |
| 4,809,679 * | 3/1989 | Shimonaka et al. ..................... 128/4 |
| 5,105,800 * | 4/1992 | Takahashi et al. ....................... 128/4 |
| 5,456,284 * | 10/1995 | Ryan et al. ........................... 137/522 |
| 5,643,301 * | 7/1997 | Mollenauer ........................... 606/167 |
| 5,879,368 * | 5/1999 | Hoskin et al. ......................... 606/185 |
| 6,053,861 * | 4/2000 | Grossi ................................... 600/154 |

FOREIGN PATENT DOCUMENTS

| | | |
|---|---|---|
| 57-53523 | 11/1982 | (JP) . |
| 58-50882 | 11/1983 | (JP) . |
| 58-50885 | 11/1983 | (JP) . |
| 59-10967 | 4/1984 | (JP) . |
| 62-23452 | 6/1987 | (JP) . |
| 5-49597 | 3/1993 | (JP) . |
| 6-125869 | 5/1994 | (JP) . |

* cited by examiner

Primary Examiner—Linda C. M. Dvorak
Assistant Examiner—Jocelyn Ram
(74) Attorney, Agent, or Firm—Greenblum & Bernstein, P.L.C.

(57) ABSTRACT

A forcep stopper of an endoscope includes an annular seal member disposed on an inlet of a channel through which a treatment tool is inserted. The forcep stopper has a circular hole whose diameter is dimensioned to be smaller than an outer diameter of a sheath of the treatment tool. The stopper is made of an elastic material such that the hole expands when the treatment tool passes through the hole. Further, a squeeze member is provided for inwardly squeezing the annular seal member from opposite lateral sides of the annular seal member in such a manner that the hole is tightly closed.

7 Claims, 9 Drawing Sheets

FORCEPS STOPPER FOR ENDOSCOPE

BACKGROUND OF THE INVENTION

1. Field of the Invention

The present invention relates to a forceps stopper for an endoscope for preventing a pressure leakage from an inlet of a channel through which a treatment tool is inserted.

The present disclosure relates to the subject matter contained in Japanese Patent Application No. Hei. 10-66521 filed on Mar. 17, 1998, which is incorporated herein by reference in its entirety.

2. Description of the Related Art

A forceps stopper of an endoscope usually has a seal member that is an elastic material, in which a closure such as a slit or the like is formed so that the closure can be spread open by means of a treatment tool to be inserted into the closure. The seal member can assume many and diverse shapes.

The treatment tools inserted into the forceps stopper for the endoscope include a forceps, a snare, a syringe, a basket and a contrast medium supply tube and the like. Such treatment tools are roughly classified into two groups, in which one uses a metallic coil pipe as a shaft and the other uses a flexible tube made of a synthetic resin.

The coil pipe has comparatively high stiffness and problems are less likely to occur when it is inserted into or detached from the forceps stopper.

On the other hand, the flexible tube does not have enough stiffness so that the flexible tube would bend by pass resistance thereof and become no longer functional when the treatment tool is passed through the slit formed in the seal member of the forceps stopper. This problem cannot be completely solved by use of the slit or other closure forming means because if the slit or the like is not formed which can be tightly closed, it is afraid that a pressure leakage would occur at an inlet of a channel through which the treatment tool is inserted.

In various seal members used today, the pressure leakage easily occurs in a seal member formed by rubber sheets having a slit formed across their thickness.

In the case of using seal members in the form of an O-ring that are squeezed in the axial direction until the hole portion is almost closed, a pressure against the passage of a treatment tool is so high that its sheath might easily bend.

SUMMARY OF THE INVENTION

An object of the present invention is to solve the aforementioned problems and to provide a forceps stopper of an endoscope so that treatment tools with a shaft that is not adequately stiff can be smoothly passed without bending and pressure leakage does not occur.

According to a first aspect of the present invention, there is provided a forceps stopper of an endoscope comprising:
an annular seal member disposed in an inlet of a channel through which a treatment tool is inserted, having a circular hole whose diameter is smaller than an outside diameter of a sheath of the treatment tool and made of an elastic material in which said hole expands when the treatment tool passes through said hole; and
a squeeze member for squeezing said annular seal member inside from opposite lateral sides of said annular seal member in such a manner that said hole is tightly closed.

According to a second aspect of the present invention, there is provided a forceps stopper according to the first aspect of the present invention, wherein a gap is formed between an outer circumference of said annular seal member and an adjacent member in a direction perpendicular to a direction in which said annular seal member is squeezed.

According to a third aspect of the present invention, there is provided a forceps stopper according to the first aspect of the present invention, wherein the surface of said annular seal member has a coating layer with low frictional resistance.

According to a fourth aspect of the present invention, there is provided a forceps stopper according to the first aspect of the present invention, wherein said annular seal member has such a cross-sectional shape that thickness of said annular seal member decreases progressively toward said hole.

According to a fifth aspect of the present invention, there is provided a forceps stopper according to the first aspect of the present invention, wherein said annular seal member has an oblong or elliptical form and said annular seal member is squeezed from a longitudinal direction of said annular seal member.

According to a sixth aspect of the present invention, there is provided the forceps stopper according to the first aspect of the present invention, wherein said squeeze member is rotated relative to said annular seal member so that said annular seal member becomes free from the squeezing force to revert to an unconstrained state.

According to a seventh aspect of the present invention, there is provided a forceps stopper according to the sixth aspect of the present invention, wherein said annular seal member has a projection and said squeeze member has a recess, wherein said projection and said recess are engagable with each other and said annular seal member is elastically fixed in a rotating direction in an unconstrained state when said projection is engaged with said recess.

According to an eighth aspect of the present invention, there is provided a forceps stopper according to the first aspect of the present invention, further comprising a tubular guide having an outside diameter larger than the diameter of said hole of said annular seal member in an unconstrained state and detachably inserted into said hole of said annular seal member, whereby an treatment tool can be inserted into or pulled out of said tubular guide.

DETAILED DESCRIPTION OF THE PRESENT INVENTION

The present invention will now be described with reference to the accompanying drawings.

Figure 12:
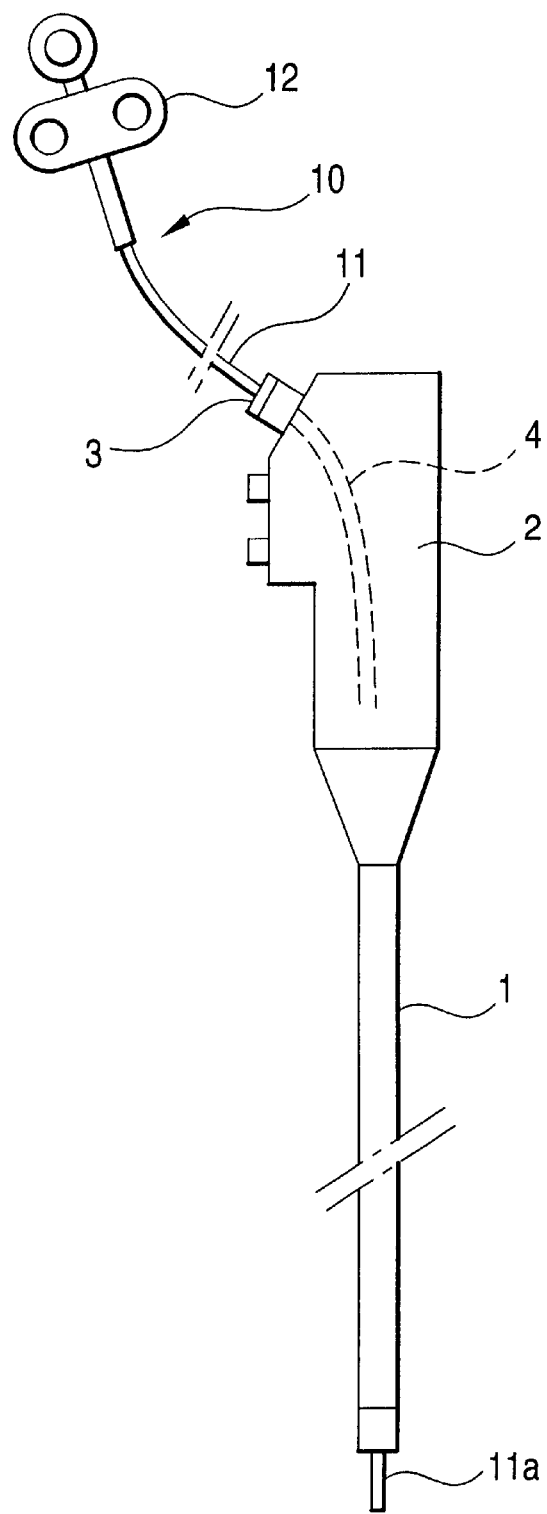
FIG. 12 is an exterior view of a treatment tool which has been set on an endoscope.

In FIG. 12, a treatment tool 10 has been inserted into a channel 4. An inserting portion 1 of the endoscope has a basal end connected to a control part 2 and a forceps stopper 3 is mounted on an inlet of the control part 2 from which the channel 4 extends toward the inserting portion 1.

A sheath 11 of the treatment tool 10 inserted into the channel 4 has a distal tip 11a projecting forward from the distal end of the inserting portion 1 of the endoscope. A reference numeral 12 shows a hand operated control part connected to the basal end of the sheath 11.

Figure 2:
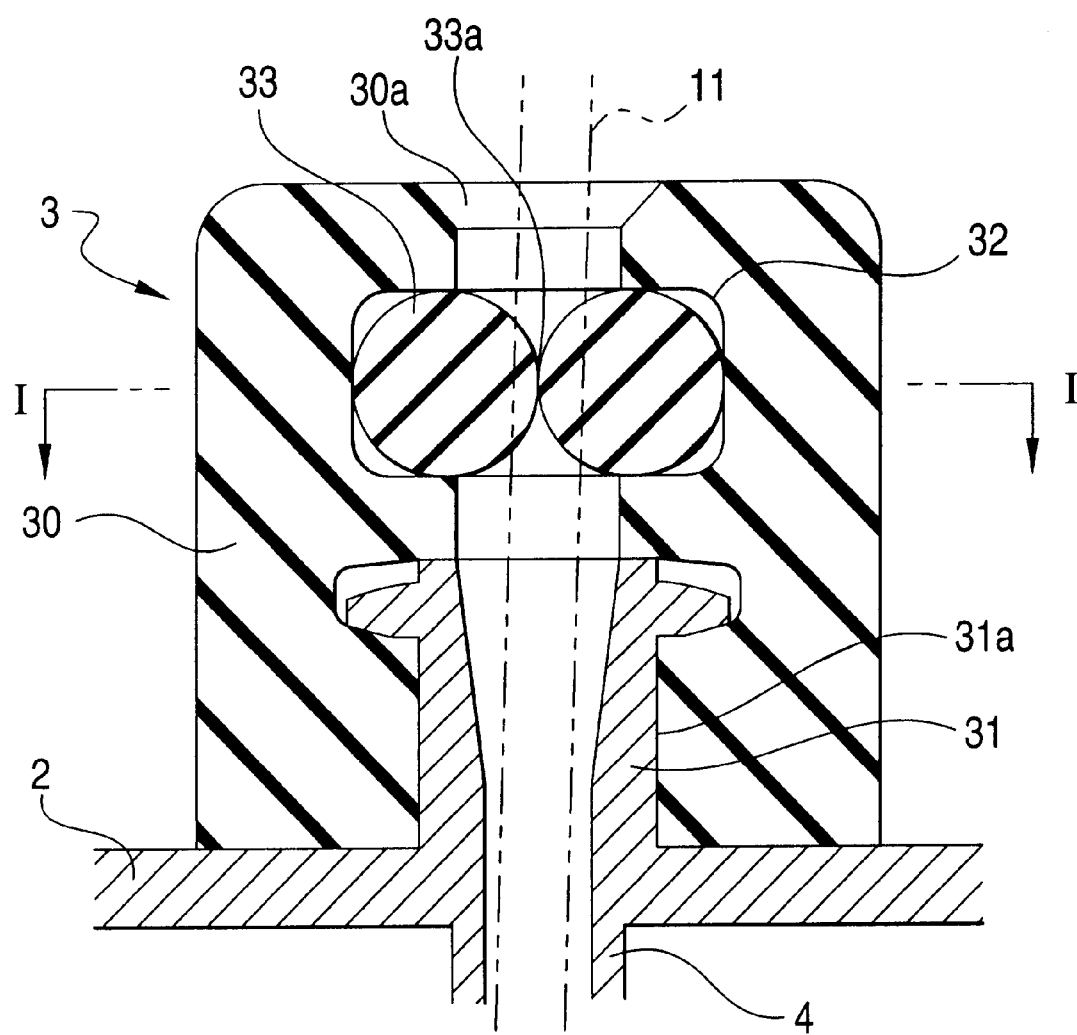
FIG. 2 shows a longitudinal section of the first forceps stopper of the endoscope of the invention.
Figure 3:
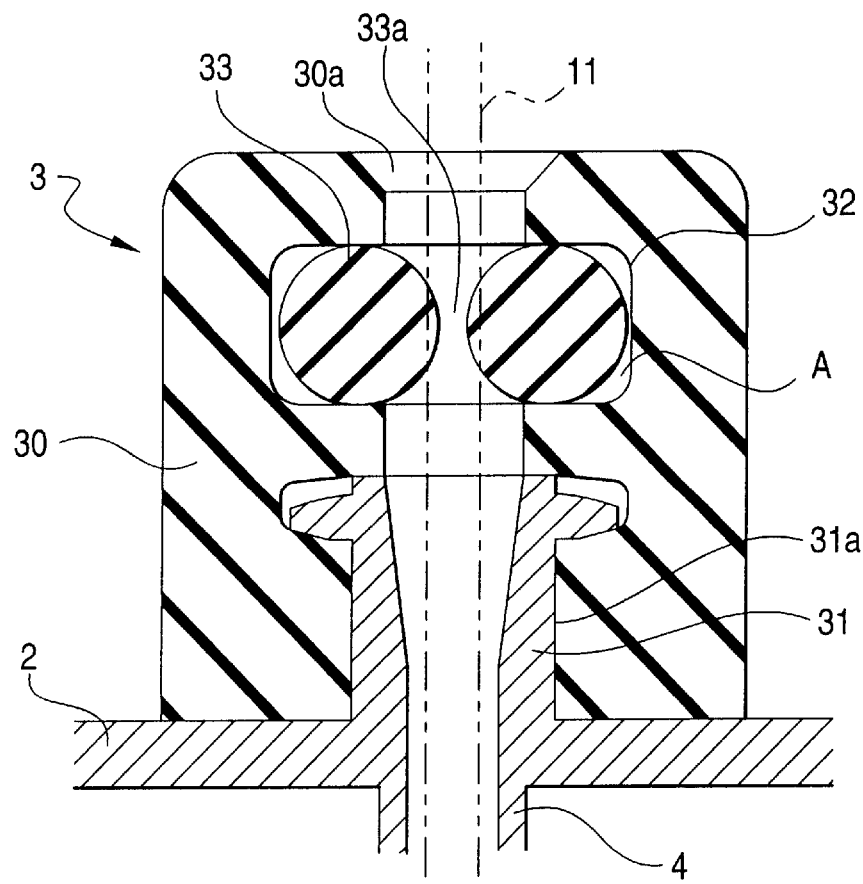
FIG. 3 shows a longitudinal section of the first forceps stopper in view of another side with the sheath of a treatment tool inserted.

FIG. 2 shows a longitudinal section of the forceps stopper 3 and FIG. 3 shows a longitudinal section in view of another side. A reference numeral 31 is the treatment tool receiving socket that communicates with the channel 4 to project from the surface of the control part 2. The socket 31 is shaped like a so-called "lure lock" male socket.

A reference numeral 30 is a stopper casing made of an elastic rubber or plastic material that is somewhat hard. The stopper casing 30 is detachably disposed in the treatment tool receiving socket 31, as an area in contact with the outer circumference 31a of the socket 31 is clamped to prevent a pressure leakage from any gap between the mating surfaces.

The stopper casing 30 has a circular seal member receiving groove 32 between an opening 30a of the casing 30 and an opening of the socket 31. An annular seal member 33 is fitted into the groove 32, which is made of a soft elastic material such as silicone rubber, nitrile rubber or chloroprene rubber.

Figure 4:
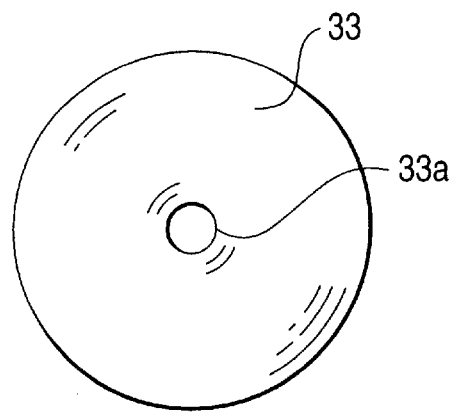
FIG. 4 is a plan view of the annular seal member used in the first forceps stopper of the invention.

When the annular seal member is unconstrained, the annular seal member 33 is shaped like an O-ring having a small hole portion 33a as shown in FIG. 4. A diameter of the hole portion 33a is smaller than an outside diameter of the sheath 11 of the treatment tool 10 which is inserted into the channel 4. The annular seal member 33 has a circular cross section as shown in FIG. 3.

Figure 1:
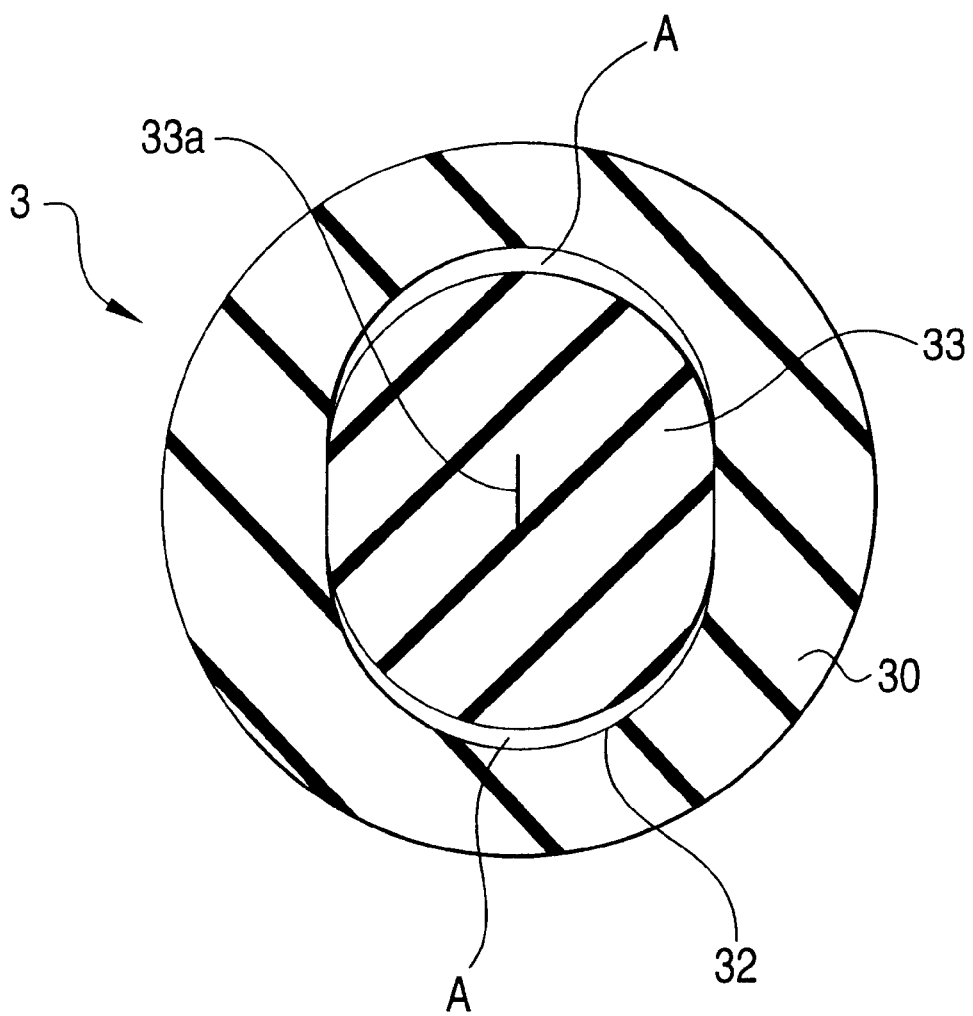
FIG. 1 shows a cross section (section I—I of FIG. 2) of a first forceps stopper of an endoscope of the invention, particularly in the area where the annular seal member is fitted in the seal member receiving groove.

As shown in FIG. 1 which is section I—I of FIG. 2, the seal member receiving groove 32 has an oblong (or elliptical) planar shape and its breadth (or minor axis) is smaller than the outside diameter of the annular seal member 33 while its length (or major axis) is greater than said outside diameter.

Because of this structural feature, if the annular seal member 33 is fitted into the seal member receiving groove 32, the annular seal member 33 is squeezed by the inner circumference of the seal member receiving groove 32, which thus serves as a squeeze member, in the direction of its breadth (or minor axis) until the hole portion 33a is tightly closed in a short straight line. As a result, there occurs no leakage of pressure from an inside of the channel 4 if the treatment tool 10 is not inserted.

In the direction of the length (or major axis) of the seal member receiving groove 32, spaces A are left between its inner circumference and the outer circumference of the annular seal member 33 as shown in FIG. 1. Therefore, if the sheath 11 of the treatment tool 10 is inserted into the hole portion 33a of the annular seal member 33, the annular seal member 33 can expand toward the spaces A, presenting only a small resistance against the passage of the sheath 11.

Figure 5:
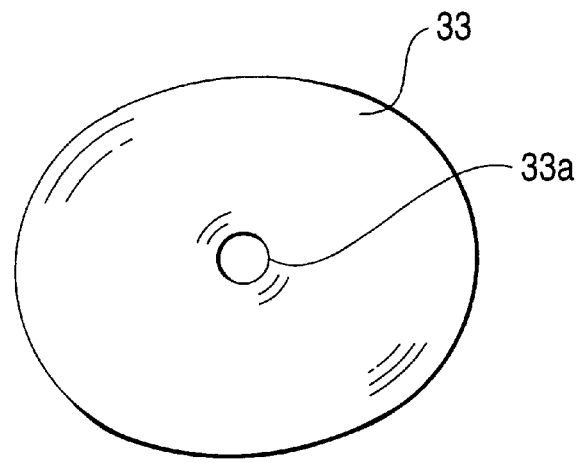
FIG. 5 is a plan view of a modification of the annular seal member of the invention.
Figure 6:
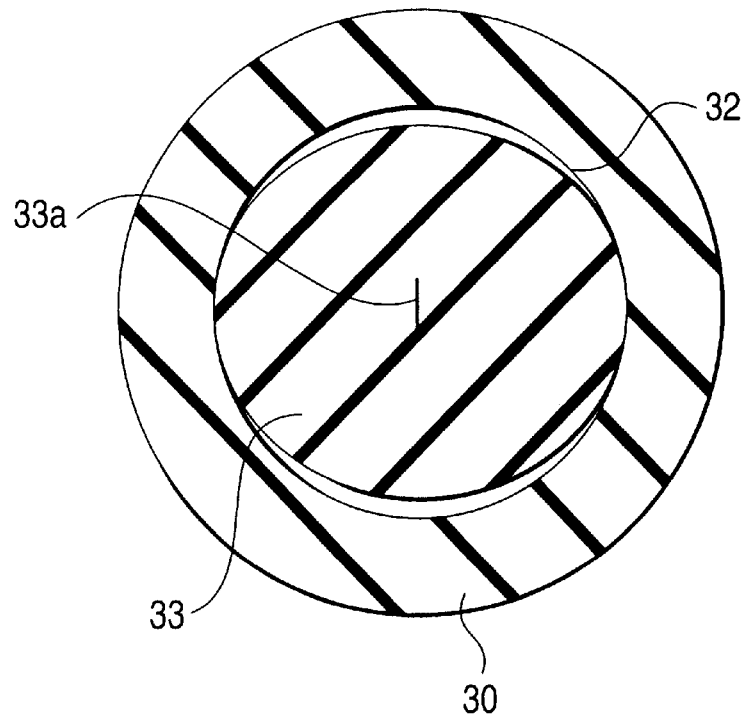
FIG. 6 shows a cross section of another modification of the area where the annular seal member which is fitted in the seal member receiving groove.

In the unconstrained state, forming the circular seal member 33 in the shape of an oblong, elliptical or other forms as shown in FIG. 5 and fitting the circular seal member 33 in the seal member receiving groove having a circular cross section as shown in FIG. 6, the circle seal member 33 may be squeezed.

When the sheath 11 is passed through the hole portion 33a of the annular seal member 33, the annular seal member 33 is spread from inside of the hole portion to the outside and the sheath 11 can be inserted into or pulled out of the channel 4 as the hole portion 33a is kept in close contact with the outer circumference of the sheath 11. As a result, there occurs no leakage of pressure from within the channel 4 even when the treatment tool is used.

Since the hole portion 33a of the annular seal member 33 has just temporarily been closed by compressive forces applied from opposite sides, only a small resistance is exerted by the seal member 33 and the sheath 11 can be inserted into or pulled out of the channel 4 without buckling even if the sheath 11 is formed of a flexible tube or other member not having adequate stiffness.

The annular seal member 33 may be provided with a coating of tetrafluoroethylene resin or other materials that are low in frictional resistance. This is effective in reducing the frictional resistance to the insertion or removal of the sheath 11, thereby preventing the sheath 11 from buckling.

Figure 7:
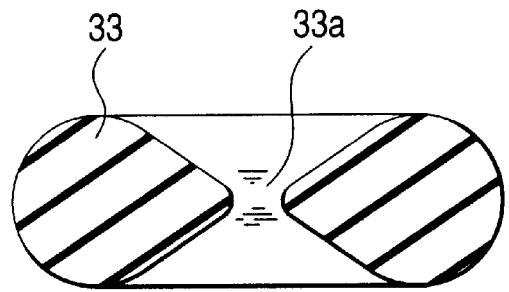
FIG. 7 is a plan view of a second modification of the annular seal member of the invention.

The annular seal member 33 may have such a cross-sectional shape whose thickness decreases progressively toward the hole portion 33a as shown in FIG. 7 and this is also effective in reducing the frictional resistance to the insertion or removal of the sheath 11.

Figure 8:
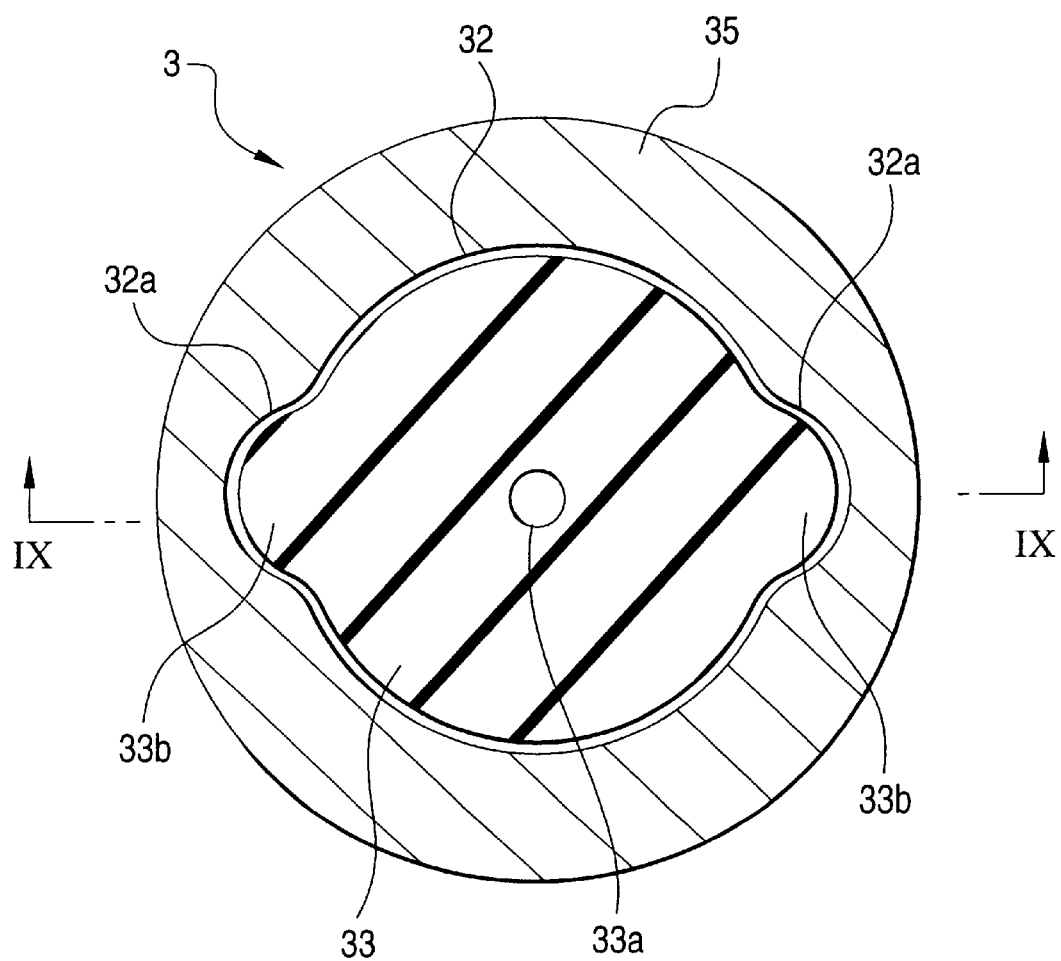
FIG. 8 shows a cross section of the second forceps stopper of the invention, particularly in the area where the annular seal member is fitted in the seal member receiving groove.
Figure 9:
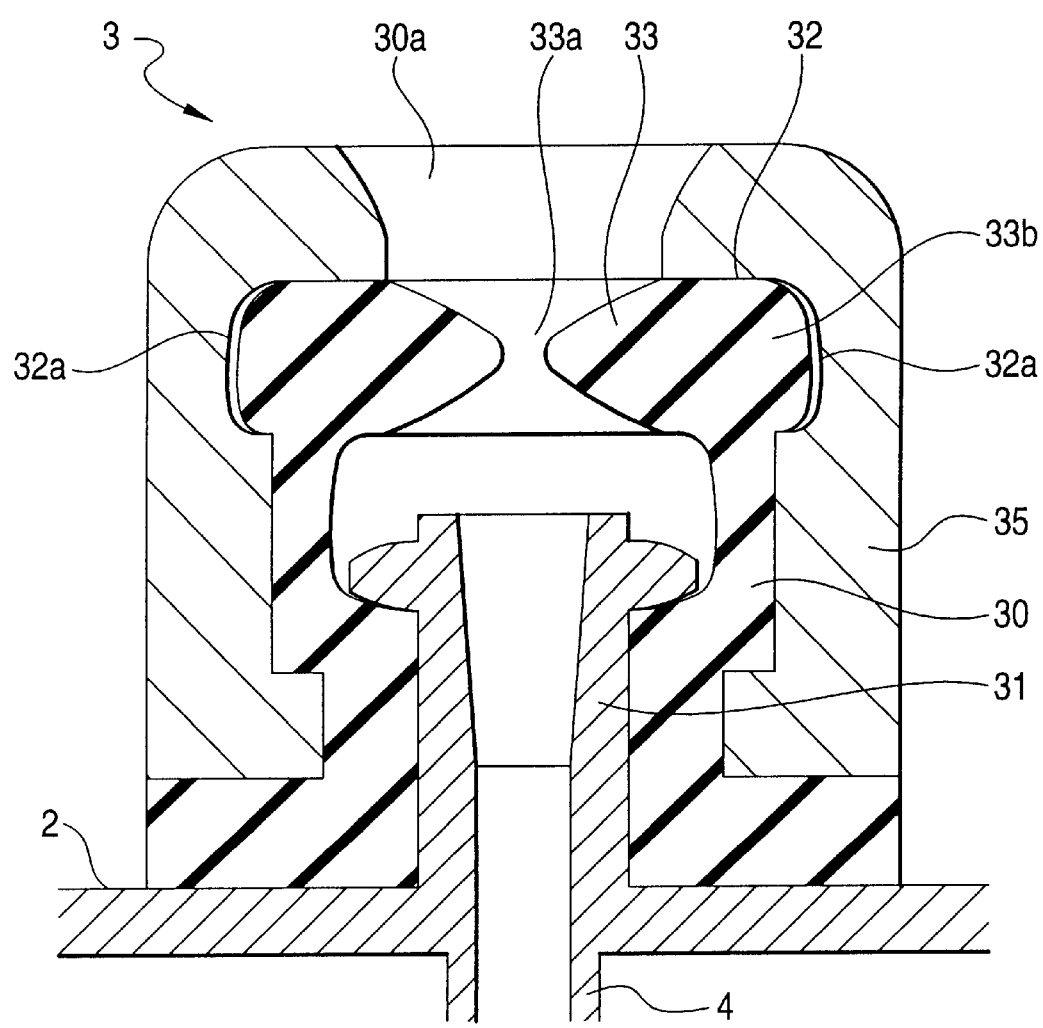
FIG. 9 shows a longitudinal section (section IX—IX of FIG. 8) of the second forceps stopper of the invention.
Figure 10:
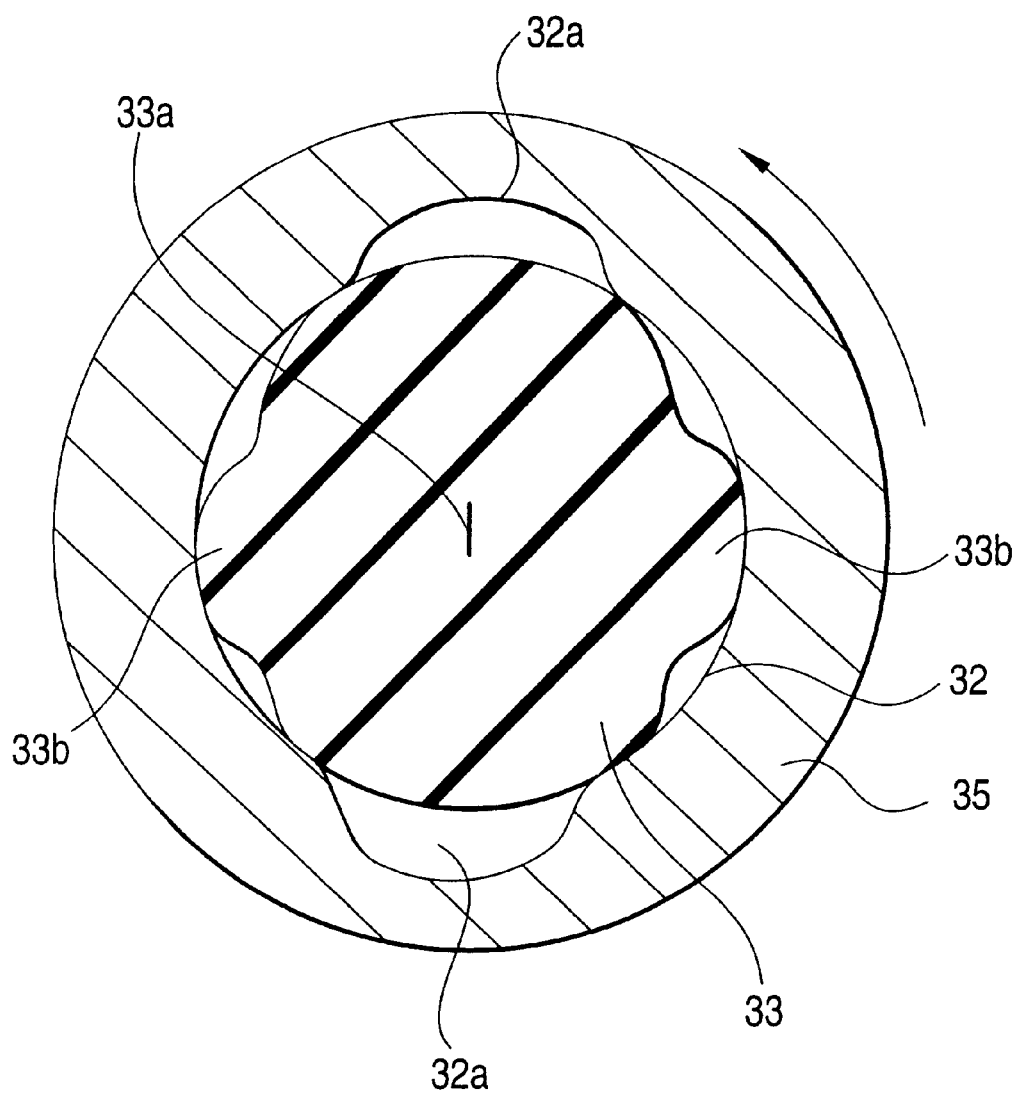
FIG. 10 shows a cross section of a modification of the area where the annular seal member is fitted in the seal member receiving groove in the second forceps stopper of the invention.

FIGS. 8 and 9 show a second forceps stopper 3 of the invention. FIG. 9 shows section IX—IX of FIG. 8. A stopper casing 30 made of an elastic material and which is detachably mounted on the treatment tool receiving socket 31 is formed integrally with an annular seal member 33 having such a cross-sectional shape that the thickness decreases progressively toward the hole portion 33a. The stopper casing 30 is enclosed with a pivot tube 35 that is fitted over the casing in such a way that it can pivot on the longitudinal axis.

A pair of outward projections 33b are formed on a brim of the annular seal member 33 in diametrically opposite positions, and a pair of recesses 32a into which the projections 33b can fit are formed on the inner circumference of the seal member receiving groove 32.

When the projections 33b are in engagement with the recesses 32 as shown in FIGS. 8 and 9, the annular seal member 33 is not pushed from any directions but remains in an unconstrained state, as the hole portion 33a is a circle of a smaller diameter than the outside diameter of the sheath of the treatment tool to be inserted into said hole portion.

In the case where the projections 33b is disengaged from the recesses 32a, the projections 33b must be deformed elastically. After the deformation, the circular seal member is elastically fixed, that is, by an effect of click.

When the pivot tube 35 turns at 90 degrees on a longitudinal axis of the pivot tube 35 from the unconstrained state, the projections 33b come out of engagement with the recesses 32a and contact the inner circumference of the seal member receiving groove 32.

The pair of projections 33b formed in diametrically opposite positions are then pressed inwardly by the inner circumference of the seal member receiving groove 32, so that the annular seal member 33 is squeezed and the hole portion 33a is tightly closed in a single line.

If there is no need to use the treatment tool or if a treatment tool with the stiff sheath is used, the hole portion 33a of the annular seal member 33 may be closed in a single line. On the other hand, in the case of using a treatment tool with a sheath that is not adequately stiff, the pass resistance of the sheath may be reduced by reverting the hole portion 33a to the circular shape.

Figure 11:
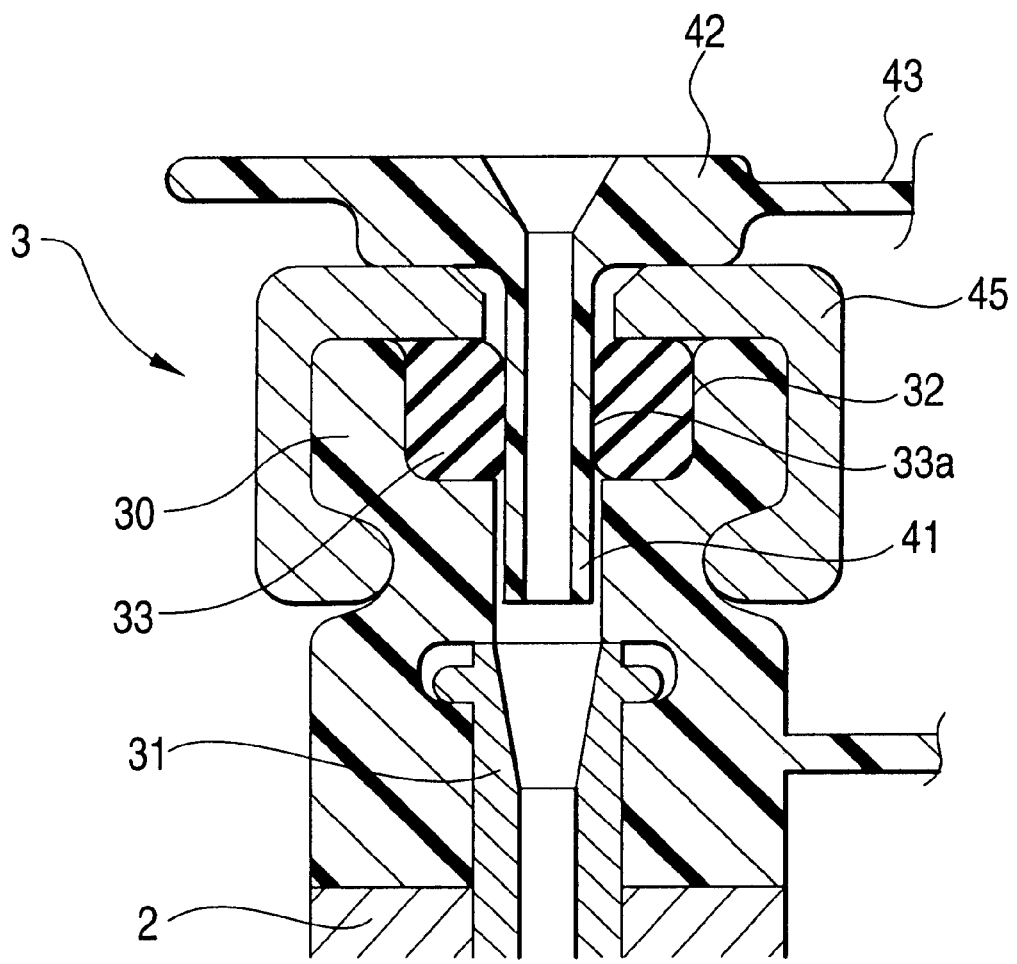
FIG. 11 shows a longitudinal section of a third forceps stopper of the invention.

FIG. 11 shows a third forceps stopper 3 of the invention. The forceps stopper 3 has essentially the same design as the first forceps stopper except a guide tube 41. The treatment tool is inserted into the guide tube 41 that is disposed in the hole portion 33a of the annular seal member 33 that has been squeezed by the inner circumference of the seal member receiving groove 32 thereby closing the hole portion in a single line.

The guide tube 41 has a protrusion 42 that can be pinched by fingers and thumb. Being connected to the stopper casing 30 by means of a string member 43, the guide tube 41 can be inserted into or pulled out of the hole portion 33a of the annular seal member 33. A reference numeral 45 is a cap that is detachably fitted over the stopper casing 30 to ensure that the annular seal member 33 would not be dislodged from the seal member receiving groove 32.

If a treatment tool with a stiff sheath is used, the treatment tool may directly be inserted into the hole portion 33a of the annular seal member 33. If using a treatment tool with a sheath that is not adequately stiff, the guide tube 41 is first fitted into the hole portion 33a and then the treatment tool through the guide tube 41 is inserted. In both of the cases, the treatment tool can be inserted into the channel 4 with a very small pass resistance.

According to the present invention, the annular seal member having a smaller inside diameter than the outside diameter of the sheath of a treatment tool is squeezed from opposite sides until the hole portion of the seal member is tightly closed in a single line, through which the treatment tool is inserted into a channel connecting to an endoscope. Because of this design, the leakage of pressure from the channel can be positively prevented when the treatment tool is not used. In addition, due to the small pass resistance, even a treatment tool with a shaft that is not adequately stiff can be smoothly inserted into the channel without buckling while ensuring a positive prevention of pressure leakage from the channel.

What is claimed is:

1. A forcep stopper of an endoscope comprising:

an annular seal member adapted to be disposed in an inlet of a channel through which a treatment tool is insertable, said annular seal member having a circular hole whose diameter is so dimensioned to be smaller than an outer diameter of a sheath of the treatment tool, said seal member comprising an elastic material, such that said hole expands when the treatment tool passes through said hole; and a squeeze member for inwardly squeezing said annular seal member from opposite lateral sides of said annular seal member such that said hole is tightly closed, said annular seal member having a cross-sectional shape such that a thickness of said annular seal member progressively decreases toward said hole.

2. A forceps stopper according to claim 1, wherein a gap is formed between an outer circumference of said annular seal member and an adjacent surface of said squeeze member perpendicular to a direction in which said opposite lateral sides of said annular member are squeezed.

3. A forceps stopper according to claim 1, wherein the surface of said annular seal member a coating layer with low frictional resistance.

4. A forceps stopper according to claim 1, wherein said annular seal member has an oblong or elliptical form and said annular seal member is squeezed from a longitudinal direction of said annular seal member.

5. A forceps stopper according to claim 1, wherein said squeeze member is rotatable relative to said annular seal member so that said annular seal member becomes free from the squeezing force to revert to an unconstrained state.

6. A forceps stopper according to claim 5, wherein said annular seal member has a projection and said squeeze member has a recess, wherein said projection and said recess are engagable with each other and said annular seal member is elastically fixed in a rotating direction in an unconstrained state when said projection is engaged with said recess.

7. A forceps stopper according to claim 1, further comprising a tubular guide having an outside diameter larger than the diameter of said hole of said annular seal member in an unconstrained state and detachably inserted into said hole of said annular seal member, whereby an treatment tool can be inserted into or pulled out of said tubular guide.

* * * * *